(12) United States Patent
Lee

(10) Patent No.: US 7,482,935 B2
(45) Date of Patent: Jan. 27, 2009

(54) BABY HEALTH MONITORING SYSTEM

(75) Inventor: Jung Kook Lee, 8008 Pinnacle Ridge Dr., Manassas, VA (US) 20112

(73) Assignee: Jung Kook Lee, Manassas, VA (US)

( * ) Notice: Subject to any disclaimer, the term of this patent is extended or adjusted under 35 U.S.C. 154(b) by 0 days.

(21) Appl. No.: 10/696,263

(22) Filed: Oct. 28, 2003

(65) Prior Publication Data

US 2005/0088296 A1    Apr. 28, 2005

(51) Int. Cl.
- G08B 23/00 (2006.01)
- G08B 1/08 (2006.01)
- A61B 5/00 (2006.01)

(52) U.S. Cl. ............ 340/573.1; 340/573.7; 340/539.11; 340/539.12; 340/539.14; 600/549; 128/903; 128/923

(58) Field of Classification Search ............... 340/573.1, 340/573.7, 539.11, 539.12, 539.14; 600/549; 128/903, 923
See application file for complete search history.

(56) References Cited

U.S. PATENT DOCUMENTS

| | | | | |
|---|---|---|---|---|
| 5,670,944 A | * | 9/1997 | Myllymaki | 340/573.1 |
| 5,904,708 A | * | 5/1999 | Goedeke | 607/18 |
| 6,033,365 A | * | 3/2000 | von Zitzewitz | 600/300 |
| 6,198,394 B1 | * | 3/2001 | Jacobsen et al. | 340/573.1 |
| 6,491,647 B1 | * | 12/2002 | Bridger et al. | 600/585 |
| 2002/0013538 A1 | * | 1/2002 | Teller | 600/549 |
| 2005/0070778 A1 | * | 3/2005 | Lackey et al. | 600/366 |
| 2007/0239038 A1 | * | 10/2007 | Nicolaescu et al. | 600/483 |

FOREIGN PATENT DOCUMENTS

| JP | 2000-217790 | 8/2000 |
|---|---|---|
| KR | 10-2002-0024083 A | 3/2002 |

* cited by examiner

*Primary Examiner*—Julie Lieu
(74) *Attorney, Agent, or Firm*—Joseph Hyosuk Kim; JHK Law

(57) ABSTRACT

The present application discloses a a baby health monitoring device comprising a skin temperature sensor connected to a microprocessor for mathematically converting the sensed temperature to corrected skin temperature; a movement sensor; a display screen for indicating condition of baby; and a means for communicating with a computer.

21 Claims, 7 Drawing Sheets

6 : Switches
7 : LCD Display
8 : Humidity Sensor
9 : Back Cover
10 : Battery
11 : Moisture Sensor
12 : Skin Temp. Sensor
13 : Heat Isolation Material
14 : Movement Sensor
15 : IR Sensor
16 : ASIC (Application Specific Integrated Circuit)
    CPU / EEPROM / Built in Room Temp. Sensor
17 : RF Circuit
18 : PCB
19 : Audio Piezo Transducer
20 : Audio Sensor

BABY HEALTH MONITORING SYSTEM

BACKGROUND OF THE INVENTION

1. Field of the Invention

The present invention relates to a baby health monitoring system for providing information for baby's health care. The present invention also relates to a monitoring device worn by a baby. The invention also relates to an electronic communication system between the device and various receivers. The invention further relates to a network system, which connects the baby monitoring device with computers at home and hospital. In addition, the invention relates to a method of detecting infection early in a microorganismic infection cycle.

2. General Background and State of the Art

First time mothers are faced with having to raise a child without the benefit of previous experience. Every parent wants to protect her child from illness. The biggest concern for a parent is when a baby has high fever. The parent often does not know what to do because she may not know whether this condition is serious or not. This causes great anxiety for the parent. Usually, when a doctor is called, one of the first questions asked is how long the baby has had the fever, and what were and are the surrounding environmental conditions of the baby, as well as a few other questions, which would have required the parent to have monitored the baby continuously to have recorded the baby's body temperature and various environmental conditions when the baby was normal, as well as during the early stages of an infection and during the full blown fever. But if the parent has not been monitoring the child continuously, it would be very difficult for the parent to provide accurate information to the doctor. The lack of accurate information weakens the opportunity of providing appropriate and timely health care to the baby.

A fever for a baby does not always mean that the baby is sick since a baby's temperature is prone to change in response to the surrounding environment or stress. Therefore, a device that continuously records the temperature of a baby and its surrounding environmental conditions, and stores this information, which is used to determine the reason for a change in a baby's temperature, would be advantageous in helping a doctor understand the etiology of a baby's illness, leading to greater possibility of correct diagnosis and care.

Thus, there is a need in the art for a system that would help parents to more easily monitor the overall health of their babies. There is a need in the art for a system that provides monitored and stored data of a baby to assist the parent and doctor in providing advantageous health care for babies.

SUMMARY OF THE INVENTION

The present invention is directed to a system to assist in the raising of children, especially a baby that is less than 3 calendar years old. The invention is also directed to early detection of onset of an infection or illness so that a parent may be in a good position to deal with the illness. The system includes a device that is worn by a baby. The device includes a temperature sensor, and optionally, a variety of other sensors.

The invention is directed to a baby health monitoring device comprising:

a skin temperature sensor connected to a microprocessor for mathematically converting the sensed temperature to corrected skin temperature;

a movement sensor;

a display screen, preferably for indicating condition of baby; and a means for communicating with a computer.

Further, the device may include a humidity sensor or sound sensor as well as other types of sensors. In one aspect, the device may be shaped as a band and may be worn on an appendage of a baby, such as without limitation, arm, leg, ankle, wrist, finger or toe. However, the device may be worn anywhere on the baby so long as the sensors are in contact with the skin and the immediate surroundings.

In one aspect, the baby health monitoring system may comprise the device described above connected to a repeater, which may be connected to a computer at home comprising software designed to communicate with the device. Further in the system, the device, repeater and computer at home are preferably connected wirelessly. In addition, in the system, the computer may be connected to a web server so as to be in communication with other computers at home or computers at hospital.

In another embodiment, the invention is directed to a method of facilitating determination of health of a baby comprising providing instructions that comprise simultaneously monitoring corrected skin temperature of the baby, monitoring ambient temperature surrounding the baby, and monitoring level of movement of the baby with the device discussed above over time; and comparing and analyzing data obtained, wherein presence of high or rising corrected skin temperature compared with substantially level ambient temperature and substantially infrequent movement indicates that the baby is not healthy. The instructions may be in written or oral form, or may be transmitted electronically.

In yet another embodiment, the invention is directed to a chart comprising corrected skin temperature profile over a set time period. The chart may further include ambient temperature profile over the set time period. Or, the chart may further include a movement profile over the same set time period. Other types of data obtained by sensor means may also be included. The chart may be displayed on a solid medium, such as a screen, a computer monitor, paper or plastic.

In yet another embodiment, the invention is directed to a method of facilitating determination of health of a baby comprising providing instructions that comprise reviewing and analyzing the chart discussed above, and comparing the corrected skin temperature profile, ambient temperature profile, and movement profile, wherein presence of high or rising corrected skin temperature compared with substantially level ambient temperature and substantially infrequent movement indicates that the baby is not healthy.

In still another embodiment, the invention is directed to a method of determining an infection or infection pattern in a baby, comprising reviewing and analyzing the chart described above, to determine a pattern or an identifying pattern of rise or fall in corrected skin temperature, which indicates the presence of an infection or an infection pattern.

In another embodiment, the invention is directed to a method of identifying a viral infection pattern comprising reviewing and analyzing a corrected temperature profile, ambient temperature profile and movement profile of a baby and comparing the data with an established profile. In this method, in one embodiment, the established profile may be provided by a computer at home or computer at hospital, and stored in a common server that links computer at home and computer at hospital.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

As used herein, "baby" is a child that is less than 3 calendar years old.

As used herein, "body temperature" is the internal temperature of a person.

As used herein, "computer at home" generally refers to a computer that is connected, preferably wirelessly, to the baby monitoring device, preferably through a repeater. Typically, the computer is placed in the home, however it is understood that the computer at home is not limited to a computer in the home of the baby, and may be placed anywhere, so long as the computer is programmed with software that analyzes the data from the monitoring device, and is able to be connected to the monitoring device, preferably wirelessly. The computer is also preferably connected to a web server that connects other computers at home and computers at hospital.

As used herein, "computer at hospital" refers to a computer that is placed at a health care center. The health care center may include a hospital, doctor's office or a clinic, so long as the health giver computer is loaded with software that is able to access the data from the baby monitoring device. Also, preferably, the computer at hospital is linked to a common or different web server with the computer at home to facilitate communication between the computers.

As used herein, "corrected skin temperature" refers to the temperature of a baby's skin as corrected by processing the measured skin temperature through a correction table, which takes into consideration various environmental factors and age of the baby.

As used herein, "normal corrected skin temperature" means the measured normal skin temperature that has been corrected and which temperature is obtained most often in a baby.

As used herein, "correction table" refers to a table containing empirical data that is used to convert a measured skin temperature to its corrected skin temperature by taking into consideration environmental factors such as ambient temperature, ambient humidity, among other such variables. It is understood that other variables may exist and may be added to further refine the correction table.

As used herein, "microorganism" refers to bacteria, virus or any eukaryotic cell or fungus. Thus, a microorganismic infection may be caused by any of a variety of bacteria, virus or eukaryotic cells.

Components of the System

Figure 1:
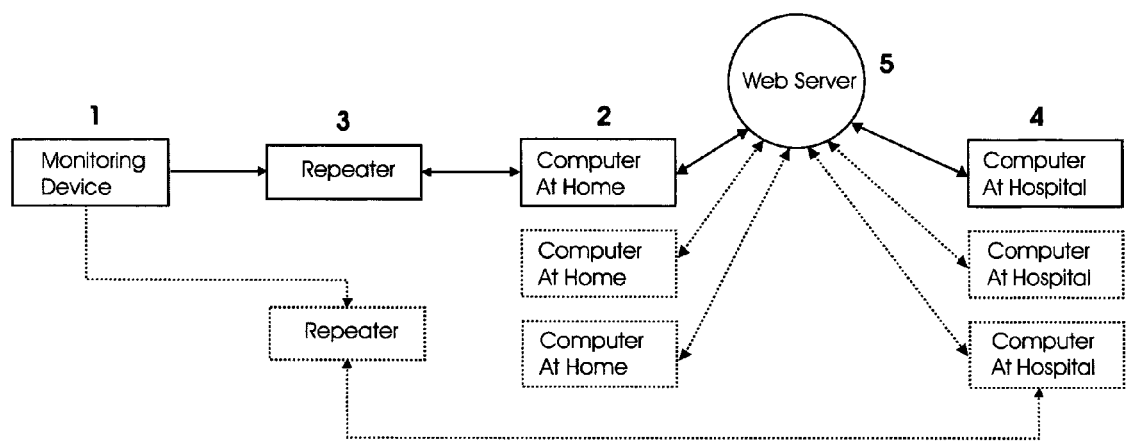
FIG. 1 shows a connected or networked system of the invention, which includes the baby monitoring device connected to a repeater, which is connected to a computer at home, which is connected to a web server. The baby monitoring device may be also connected to a repeater, which is connected to a computer at a health care center, such as a doctor's office or a hospital, which is also connected to a web server.
Figure 2:
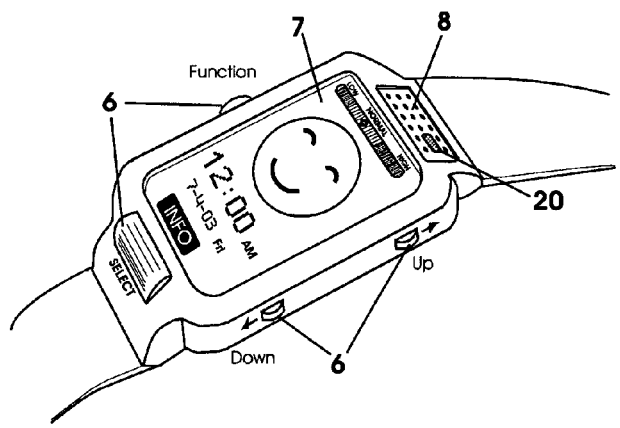
FIG. 2 shows a rendering of the monitoring device, with a switch (6), a display (7), and humidity sensor (8).

As shown in FIG. 1, the present system is comprised of:

(1) A baby health monitoring device worn by a baby. In one aspect, it may be in the shape of a band, such as a wristband or a wristwatch (FIG. 2). However, it is understood that any shape device may be used, so long as the device contacts the skin. The condition of the baby may be displayed on the face of the device in the form of words, numbers or icons. It is understood that the monitoring device alone may comprise the system of the invention. However, other elements may be included.

(2) Optionally, the system may include software and personal computer used at home, whereby the software is installed on the personal computer at home. The device may be connected by a wireless network to the computer, or the information on the device may be downloaded directly onto a computer. The software may communicate with the monitoring device, and may analyze the downloaded data obtained from the device. The software provides data analysis capability and ability to share information with other computers, optionally through a network.

(3) Optionally, the system may include a repeater, which connects and may work as a bridge between the device and the personal computer.

(4) Optionally, the system may include software and hospital computer used at the hospital, whereby the software is installed on the hospital computer at the hospital, which software strengthens the function of the system. The device may be connected by a wireless network to the computer at hospital, or the information on the device may be downloaded directly onto a computer such as by plugging the monitoring device into the computer. The software may analyze the data downloaded on to the computer from the device. For example, when the baby visits a hospital or doctor's office, the sensory input data stored in the device or computer at home may be transferred to the computer at hospital so that the doctor may review and analyze the data.

(5) Optionally, the system may include a web server, which manages and controls the monitoring device, personal computer, and the hospital computer so that they are interconnected and information may be shared.

Functions of the System

The monitoring system senses, processes, records, stores and uses physiological and environmental information to provide optimum health care for babies.—The present invention is generally directed to an environmental sensing means as it relates to a baby, and keeping records of the sensory input data so as to determine whether the baby is healthy or not. Further, the invention is directed to making a computer network that allows for sharing of information and software to analyze the data obtained.

Generally, a comfortable environment for humans falls in the temperature range of 22~25° C. and humidity range of 40~60%. Conditions of the surrounding environment are even more important for babies as they have not yet developed adaptative mechanisms to their surroundings. For adults, small environmental changes are not a big problem, but it could cause problems for very young children as they are more sensitive to changes in their surrounding environment. For instance, mothers tend to cover their babies with warm blankets out of fear that their babies may catch a cold. But in such a situation, the baby may be overheated, leading to heat rashes and concomitant secondary infections. Therefore, because babies do not tolerate environmental extremities very well, virtually all babies are raised in relatively mild, comfortable surroundings.

The monitoring system of the invention can monitor the surrounding environment of a child continuously, and if it detects environmental conditions that may harm the child, it will inform parents so that they can adjust the environment properly. The monitoring system may also provide other information or timed reminders and records that are necessary for raising children such as scheduling doctor's visits according to their ages, such as for vaccinations and so on.

The monitoring system monitors the baby's skin temperature continuously, and optionally may monitor baby's sleeping hours and activity hours as well, and provide information on the status of the baby, which data may be used to detect any abnormality.—The quickest and best way to diagnose a baby's health condition is by measuring the baby's body temperature. Fever is a natural defense mechanism by the body against bacterial or viral infections. Such fever is often more severe for new-borns or babies who have not developed the ability to control their body temperature. Neglecting high or low temperature could lead to adverse medical conditions such as convulsions or brain damage. Thus, to avoid such a disaster, periodic measurement of the body temperature of the baby is recommended. It is especially more important for younger children since new-borns or toddlers with underdeveloped immune system are more vulnerable to infections.

A baby's sleeping hours are very long. For instance, new-born babies sleep 18~22 hours a day until they reach 6 months old, and 6 to 12 month old babies sleep 2~3 hours less than that. In the beginning of a baby's life, mothers can observe the baby all the time, but later it becomes practically more difficult for mothers to be always with their babies. Thus, it is not easy to monitor the baby's temperature continuously.

The inventive monitoring system continuously monitors a baby's skin temperature and converts the skin temperature mathematically to its corrected skin temperature, and the data is analyzed to determine whether the fever is due to conditions of the surrounding environment, temporary stress, or an infection. Thus, the inventive monitoring device not only measures the temperature itself but also measures and continuously monitors the changes in the corrected skin temperature, which is actually more important for determining whether there is an infection than knowing an isolated temperature value at any given moment in time. Further, a typically age-specific normal range of values and patterns for such parameters as corrected skin temperature, activity, and so on can be pre-stored on the monitoring device or the computer at home or computer at hospital so that when the measured sensory input data falls outside this range, then a warning signal can be sent. The system may further optionally provide steps to remedy the situation in response to the specific conditions.

The temperature of humans fluctuates periodically within a 1° C. range between morning and evening. Also, a baby's temperature is a little higher than that of an adult and as the baby grows, the temperature decreases gradually and eventually reaches adult temperature. Thus, the presence of fever can be more accurately determined by measuring the magnitude and/or pattern of change in temperature of a baby rather than relying on the temperature at a given moment in time.

The inventive monitoring system monitors the change in the corrected skin temperature continuously and stores the data. Along with the changes in the corrected skin temperature, the sleeping and activity hours, as well as crying pattern may also be monitored, stored, and considered as factors to determine the health condition of babies.

With regard to the audio sensor detecting the crying sound of a baby, it is known that the audible range for humans is in the range of 20 Hz to 20 KHz, but the most audible sound is at around 4,000 Hz. Within or about this frequency is the sound of baby crying among other types of sounds. The audio sensor may be used to filter out all other sound frequencies except for around 4,000 Hz to better measure and focus on the baby crying sound. A baby usually will cry for a reason, and therefore measuring the duration of the crying, and comparing this sensory input data with the other types of data such as corrected skin temperature, activity, ambient temperature and so on will be helpful to interpret the data in totality to better understand the health of the baby.

Even though it is very important to know the normal temperature of an individual baby in order to understand the significance of any temperature increase, generally, parents do not measure their baby's temperature unless the baby becomes sick. Therefore, the normal temperature reference point is frequently not available. As a result, it is unusual for parents to be able to detect abnormal conditions of their babies unless the baby is very sick or the temperature is very high. Thus, in one aspect of the invention, the inventive monitoring system detects abnormalities early in the illness cycle with fine sensitivity to changes in the baby's physical condition, based on continuous and periodic measurement of the corrected skin temperature, optionally in conjunction with other indicators.

The condition of the baby can be read directly from the baby monitoring device and thus a parent or doctor may be immediately informed if any abnormal condition is detected.—When an abnormal condition of a baby is detected, this can be transmitted online to a computer at hospital. The computer at home or computer at hospital can also communicate with a cell phone. The doctor who has received information about the baby through the computer at hospital can inform parents about more exact diagnosis and rapid treatment if need be.

Figure 10:
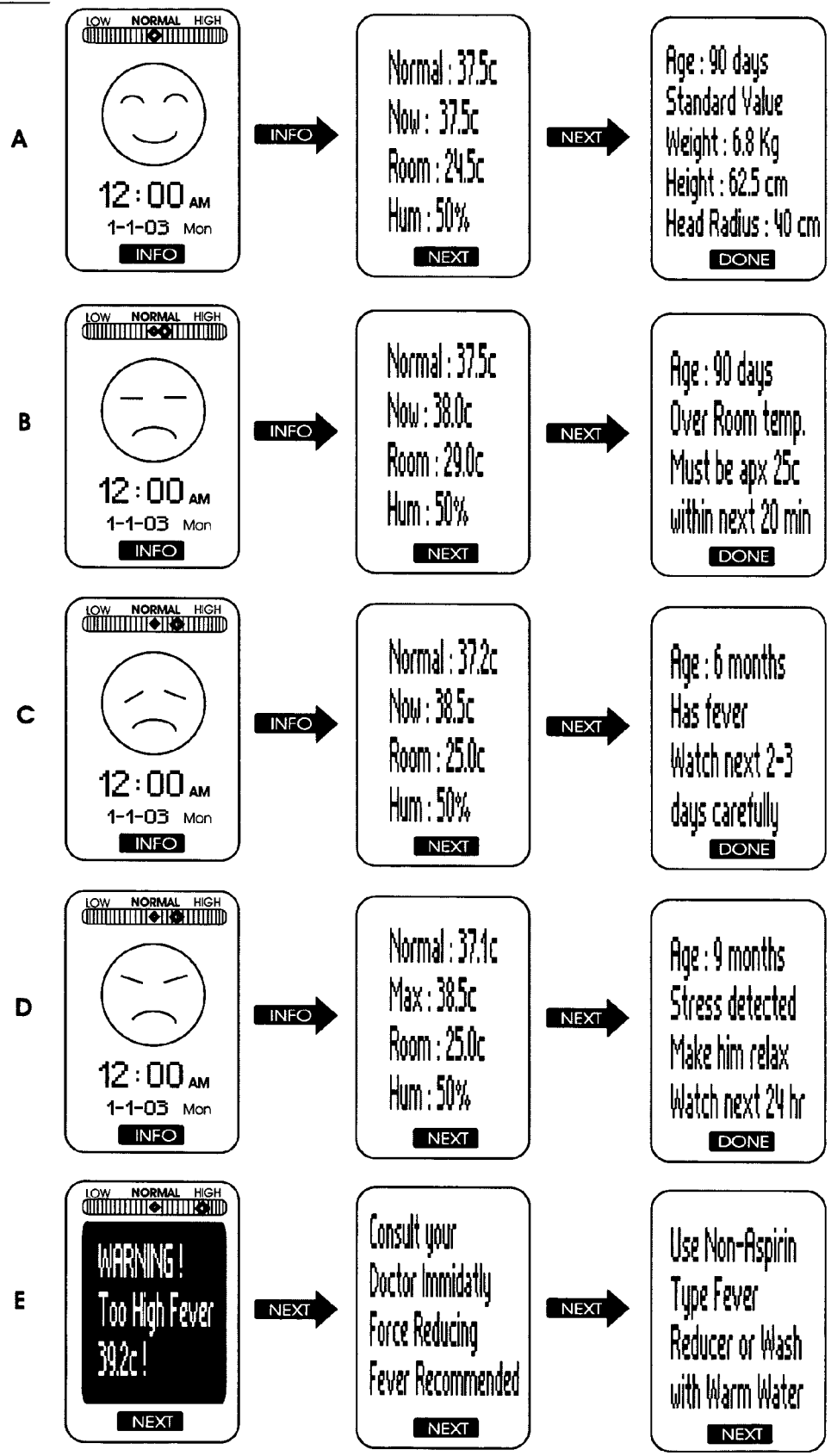
FIGS. 10A-10E show various icons that may be displayed on the baby monitoring device to show health condition of the baby.

In one aspect of the invention, the display on the monitoring device worn by a baby may display the condition of the baby in words, numbers or icons, so that the condition can be recognized easily at a glance. (FIG. 10)

Data transmitted from the monitoring device to the computer at home may be continuously stored on a memory device, permanent or temporary, such as a hard disk of the computer so that the records may be reviewed and analyzed more easily. These records in electronic or hard copy format can be transmitted to a doctor whenever desired or may even be sent automatically for example, during emergency or on a regular basis, such as once a month. Parents often call a pediatrician when their baby is not well to ask for advice, but if parents transmit such data regarding their baby to the doctor, the doctor will be able to review the history of the baby's corrected skin temperature as well as the environmental conditions correlating with the temperature data. This will allow the doctor to access a much more comprehensive information about the baby's health, which results in more accurate diagnosis of the baby's condition, having the full information at his disposal.

Early detection of known diseases or infection is possible.—Fever usually starts with a bacterial or viral infection, but there are various other diseases that are accompanied by fever. The intensity and timing of the fever may vary depending on the type of infection. Usually, the temperature changes within intervals of several hours. For example, in case of Herpes Virus 6 infection, the temperature fluctuates between 37.5° C. and 38.9° C. during the first two days after the onset of infection. Such changes in temperature is an important indicator for determining the causative agent of the fever and the condition of the patient. In fact, forced alleviation of the fever by an anti-fever agent may make diagnosis and treatment of the patient more complicated. Also, it is known that the body fights infections better when there is a fever. For these reasons, it is common sense not to use an anti-fever medication unless the fever is very high. Doctors also recommend just watching the condition of the baby for several days unless the fever of the baby reaches emergency levels.

Until now, it has been almost impossible to diagnose a disease or an infection by employing hardware and software without doctor's direct examination. Regardless of the age, for adults or children, viral infection involves characteristic symptoms which doctors rely upon to make their diagnosis. Such common symptoms are more distinct for babies and are readily recognized because typically, babies' immediate surrounding environments are usually similar as well as their various physical characteristics. Thus, diagnoses regarding infections are predictive from baby to baby.

In one aspect of the invention, the monitoring system takes advantage of these common growth environment and physical characteristics among babies and generates a characteristic infection pattern (IP) for the disease or infection. An infection pattern is generated by continuously monitoring the duration and degree of the fever, sleeping hours, movement, and optionally crying pattern or perspiration level of the baby according to its age and gender, as well as other specific characteristics. The infection pattern includes not only the status of the baby after onset of the illness, but also includes the baby's condition before the onset, and during the incubation period. Once the infection pattern is obtained, early diagnosis of the disease becomes possible by pattern match method. The infection pattern obtained from the subject baby may be compared with a database of infection pattern to find its match and thus identify the type of infection.

A baby's body is sensitive and can show some symptoms of infection, even some outward activity during the incubation stage. However, until now, any symptomatic activity occurring during this incubation stage has been neglected to be measured. There is a high probability that symptomatic activity during the transition period from the incubation phase to outbreak period will be manifest in a baby. Thus, the infection pattern also includes changes in baby's condition during the incubation and transition periods. The generated infection pattern provides profiles of changes in physical condition of the baby during incubation, transition and early outbreak periods as well as during the outbreak period.

The generated infection pattern is compared to the empirically constructed infection pattern database of illnesses in order to diagnose the illness. This type of diagnosis may be a preliminary diagnostic tool since it is diagnosis obtained during the early stage of the outbreak. With the diagnosis of the disease, treatment suggestions for the disease and other information may also be transmitted to parents.

As more people use the baby monitoring system, the infection pattern data will accumulate and thus diagnosis based on matching the infection patterns will become more accurate as data are continuously collected and confirmed, especially during the incubation and transition periods. This indicates that it is possible to preliminarily diagnose an illness at its very early stage using an infection pattern that is determined by taking into consideration the pattern of corrected skin temperature, movement, ambient temperature and other sensor inputs, even before outward distinct symptoms of the illness have manifested.

Online networking strengthens various functions of the system.—Although the system possesses infection patterns of known disease symptoms, it is also possible to diagnose new epidemic illnesses online. Computer at home and computer at hospital may be connected to the server and may be updated with new information. Thus, the system may check a baby's infection pattern after it receives infection pattern data of an epidemic illness online and if the baby's infection pattern corresponds to or is in progress toward infection pattern of an epidemic illness, informs the doctor of this diagnostic data. In another aspect of the invention, the monitoring device may display symptoms and comments for a particular condition, if the condition is recognized to be a particular type. For example, the display may read: Rash on face and diarrhea, it will go away in 3~4 days.

According to one aspect of the invention, the infection pattern (IP) is generated not only during the infection, but is generated continuously. Thus, for example, the various profiles of the baby for the last 30 days may be generated. Parents with the monitoring system and doctors with computer at hospital may share the infection pattern of a baby who has a new disease online with other parents. For example, a submitted IP is automatically downloaded to all computers at home and computers at hospital connected online so that the data may be compared with IP of other babies. This mechanism enables early diagnosis of any possibly new epidemic of infections.

The monitoring system requires that the baby's personal data be entered accurately from the beginning, such as birth date, gender, place of birth, blood-type, and so on. However, it is understood that such personal information is not limited to those listed herein. Any type of personal information may be included. It is possible to use this type of personal information so that age-specific, gender-specific, or even blood-type-specific messages may be received or sent online to the monitoring device and/or the computers at home or hospital. For instance, the hospital can send notices online automatically according to the child's age (Example: Your baby's vaccination is due on June 15). Advertisers can also send advertisements online (Example: Proper food for 1-year old baby). Parents can communicate with other parents who have children of similar age. In another aspect of the invention, the monitoring system may also have other functions such as making online appointments with a doctor. Also, one can also send a birthday card for a friend's baby. All of these functions may be automatically performed by online connection.

Body Temperature

Standard body temperature is the temperature of the rectum measured 6 cm inward from the anus. However, it is clinically difficult to measure the temperature in the rectum every time, so the temperature of the armpit is usually measured. However, it takes at least 20 minutes to reach constant temperature in the armpit. Usually, oral temperature is taken and it is measured by holding the thermometer under the tongue with mouth closed. In this method, since constant temperature is reached in about 5 minutes, clinically, this is convenient. When healthy people are in stable condition, oral temperature is 0.6° C. lower than the rectum temperature, and the armpit temperature is 0.2° C. lower than the oral temperature. Normal body temperature of humans is 36.9° C. by the armpit temperature and there is little difference in the body temperatures between Orientals and Caucasians. Children's temperature is a little higher than that of adults and that of old people tend to be low. However, there is little difference between men and women's body temperatures. There are changes in the body temperature during the day; the lowest between 4-6 a.m. and the highest between 6-8 p.m., with the range of the difference within about 1.0° C. The exact reason for this cyclic difference in body temperature is not yet known, but one possible reason may be heat generated during day time and inactivity at night, which does not generate heat.

Adults have a well-developed temperature control mechanism. In adults, a mechanism for maintaining constant body temperature involves controlling the release of heat from the body primarily by blood circulation. When the internal temperature of a body is too high, blood circulation increases to carry the heat to the skin, whereby the heat is dissipated to the environment. As a result, skin temperature rises due to increasing amount of blood flow to the skin. Conversely, if the internal temperature of a body drops, the blood vessels in the skin contract, which results in a decrease in skin temperature due to the reduced amount of blood to the skin. That is, when the temperature of the skin is measured, what is in essence measured is the temperature of the blood flowing to the skin, which is also related to the amount of blood delivered to the skin. Other environmental factors, such as age and humidity, ambient temperature and so on are taken into consideration when determining the corrected or real temperature of the skin.

In this regard, compared with adults, babies do not have a well-developed temperature control mechanism. In adults, the skin temperature may provide a distorted temperature data from their body temperature because the body may attempt to compensate and regulate its temperature by sending more or less blood in reaction to the environment or an infection. In adults, the internal body temperature is the reliable indicator. Therefore, skin temperature in adults is not a sensitively reliable health monitor. In babies, on the other hand, the amount of blood flowing to the skin is fairly constant, much more constant compared with an adult, no matter what the environmental or internal circumstances are. The skin temperature of a baby is representative of and correlates well with its internal body temperature. Thus, babies are ideally suited for measuring their skin temperature as one of the monitoring parameters for their health.

In addition, one common feature among babies is that their growth environments are similar, that is, they are generally not exposed to extreme environments. As a result, for babies, skin temperature data combined with other sensory input data, in particular regarding environmental conditions, is reliable enough to be useful in monitoring the health of a baby such as in detecting infections and patterns of infection. Thus, in one aspect of the invention, although the skin temperature can be correlated to the internal body temperature of an adult or baby (for adults it is much more difficult because of its ability to self regulate its temperature) by multiplying the skin temperature by some empirically determined factor, in the case of a baby, this type of mathematical manipulation of converting skin temperature to body temperature is not necessary. Accurate and reliable skin temperature of a baby can be determined and is useful because of the constancy of a baby's immediate surroundings. A baby typically does not go through extreme environment changes, and also the baby does not have a well-developed temperature control mechanism. Therefore, measuring the skin temperature and correcting for certain environment conditions is a dependable indicator of the health of a baby. Thus, in one aspect of the present invention, to avoid potential errors caused by mathematically converting the measured skin temperature to the internal body temperature, the present invention is directed to mathematically converting the measured skin temperature to the corrected skin temperature, which is used to operate various functions of the inventive monitoring system.

Knowledge of a baby's individual corrected normal skin temperature at certain time points throughout the day is important so as to be a reference point to interpret changes in the corrected skin temperature. Because the normal temperature of a baby, as well as adults, changes periodically between day and night, the normal temperature will not be a fixed number depending on the time of day and perhaps other factors. A person's normal temperature must be determined individually. For instance, doctors recommend measuring temperatures of the same body part at the same hour for comparison. That is to say, obtaining the difference in temperature is more important than obtaining any measured temperature value in isolation. Thus, it is necessary to determine an individual's normal corrected skin temperature in the practice of the invention so as to provide the reference point.

Determining Corrected Skin Temperature and Normal Corrected Skin Temperature

In one aspect of the invention, an accurate measurement of the skin temperature is desired. The age of the baby, as well as such factors as ambient temperature surrounding the baby, humidity and amount of perspiration should be considered to obtain the skin temperature accurately. An electrically erasable programmable read-only memory (EEPROM) in the monitoring device contains a correction table, which includes the relationship between skin temperature and age of the baby and several environmental factors to arrive at the corrected skin temperature. The measured skin temperature from the monitoring device is converted to a corrected skin temperature based on the correction table stored in a database. Basically, all of the functions of the baby monitoring system operate based on the corrected skin temperature, rather than the body temperature. In this regard, the contents of U.S. Pat.

No. 6,547,745, as it relates to the general concept of a "look-up correlation table" is incorporated by reference herein.

Using appropriate software, the baby monitoring system calculates the difference in corrected skin temperature by automatically tracing the variations in the normal corrected skin temperature correlated with time, and comparing it with the corrected skin temperature obtained for a given reading.

However, for users who are more familiar with internal body temperature rather than skin temperature and who desire to ascertain the body temperature, the converted internal body temperature may be displayed on the display screen of the monitoring device or a computer monitor by multiplying the corrected skin temperature by an empirically determined conversion factor. Since babies have a much more uniform physical characteristics than adults, the conversion factor tends to be consistent from baby to baby. The conversion factors for converting the corrected skin temperature to body temperature also may be stored in an EEPROM. The conversion factor may change with respect to the age of a baby and the correction table may be adjusted for it. If one needs to know more accurate body temperature, individual calibration would be required depending on each baby. Thus, it is possible to find a relatively accurate body temperature, if this is desired. However, for purposes of the present invention, the corrected skin temperature determinations alone are sufficient to practice the invention. Further, in the present invention, the mathematically converted body temperature, if used, may be for display purpose only, and is not stored.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Monitoring Device

Figure 3:
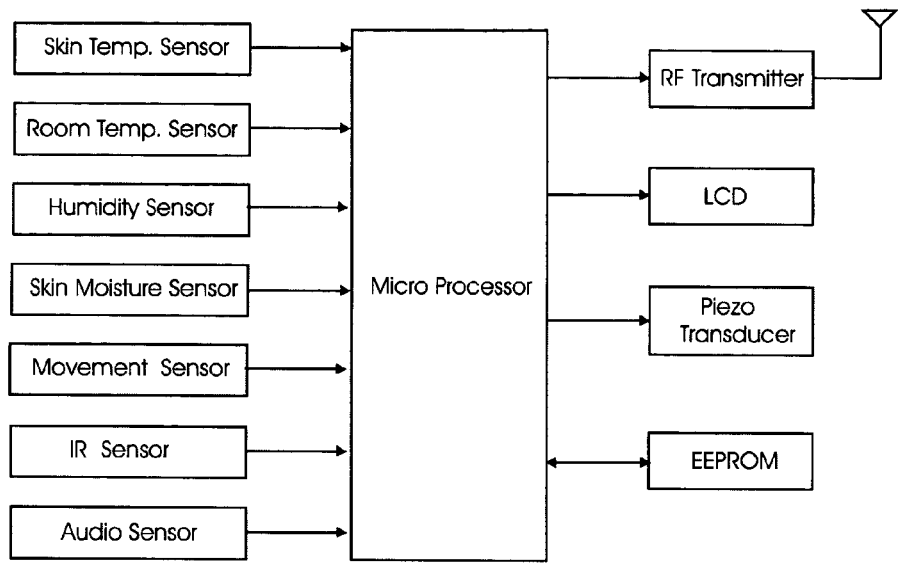
FIG. 3 shows a block diagram of the connectivity between the sensors in the monitoring device with a microprocessor, which is in communication with EEPROM, RF transmitter, display, and piezo transducer.

FIG. 3 shows a block diagram of THE MONITORING DEVICE.

Figure 4:
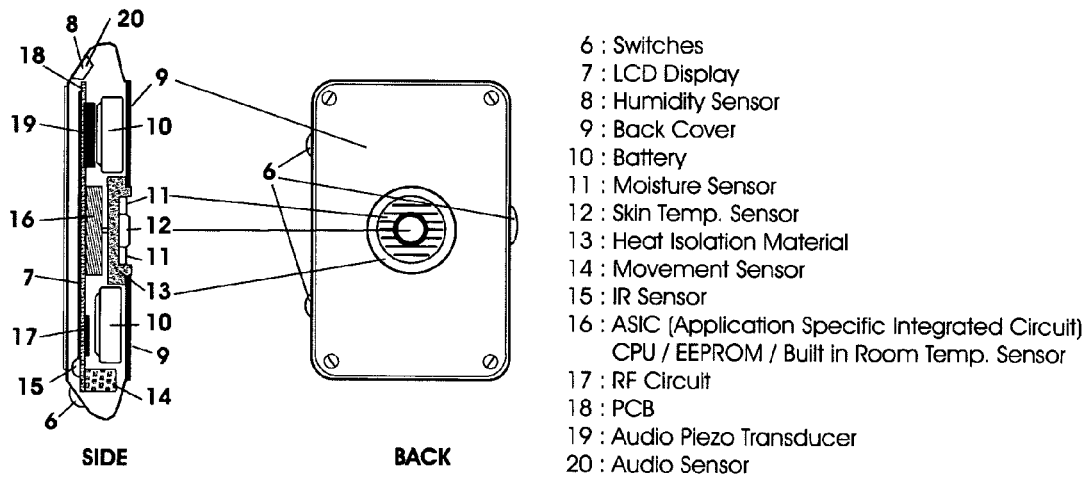
FIG. 4 shows a rendering of the baby monitoring device, including switches (6), display (7), humidity sensor (8), back cover (9), battery (10), moisture sensor (11), skin temperature sensor (12), heat insulator material (13), movement sensor (14), infrared (IR) sensor (15), ASIC (Application Specific Integrated Circuit) CPU/EEPROM/built in ambient temperature sensor (16), radio frequency (RF) circuit (17), printed circuit board (PCB) (18), audio piezo transducer (19), audio sensor (20).

THE MONITORING DEVICE, which may be shaped without limitation like a wristwatch or a wristband, may comprise a thermal sensor to detect baby's skin temperature, a digital thermometer for measuring the immediate surrounding temperature, a microprocessor, EEPROM, moisture sensor for detecting perspiration, a humidity sensor for measuring atmospheric humidity, LCD display, movement sensor for sensing a baby's activity, audio sensor to detect the sound of baby crying, IR sensor, battery, RF circuit, piezo transducer and a few control switches, as shown in FIGS. 2 and 4. To conserve a baby's skin temperature, the back cover is made of insulating material with high heat resistance as well as skin care material for a baby's delicate skin.

Although it is possible to program THE MONITORING DEVICE using control switches shown in FIGS. 2(6) and 4(6), preferably, the computer at home may be used to carry out various functions. In an exemplification, the data obtained from the device are transmitted to the computer at home through a communication port (example, IR) of THE MONITORING DEVICE. Conversely, certain data may be transmitted from the computer at home to THE MONITORING DEVICE. In general, the communication port is used whenever software update is necessary or new infection pattern information such as for a newly discovered virus is desired to be downloaded on to the computer at home or uploaded on to THE MONITORING DEVICE. However, it is understood that the invention is not limited to using an IR means for communication between the device and the computer. Alternative ways for transmitting electronic data are contemplated and are included in the present invention.

A baby's identification contains birth date, blood type, gender, telephone and home address. This identification may be used not only for data transmission but also to analyze the baby's current condition comparing baby's temperature profile with baby's age. THE MONITORING DEVICE may be worn on an arm or an ankle or any appendage or on any part of the body so long as the device contacts the skin.

Figure 5:
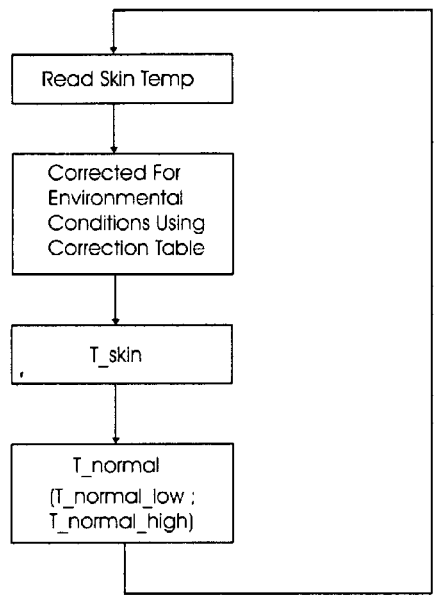
FIG. 5 shows a flow chart of how a corrected skin temperature is obtained and how normal corrected skin temperature values are obtained. "T-skin" is corrected skin temperature. "T_normal" is normal corrected skin temperature. "T_normal_low" is low normal corrected skin temperature. "T_normal_high" is high normal corrected skin temperature.

FIG. 5 shows methods of finding normal corrected skin temperature of a baby (measuring time interval: 12 minutes). Initial skin temperatures measured by the thermal sensor shown in FIG. 4(12) is corrected based on a correction table stored in EEPROM, which includes a database analyzing correlation of the skin temperature with environmental factors, such as the immediate surrounding temperature, humidity, and amount of sweat. Since the skin temperature of a baby is affected by these environmental factors, these factors should be considered for determining the corrected skin temperature accurately.

Although the body temperature of a baby may be used to practice the invention in obtaining various data and creating body temperature charts and so on, the present application exemplifies using corrected skin temperatures, as the present invention may be practiced with knowledge of the baby's corrected skin temperature and not necessarily requires ascertaining the internal body temperature of the baby. The present invention involves measuring the change in the corrected skin temperature, therefore, ascertaining an exact internal body temperature is not required.

The normal corrected skin temperature (T_normal) is the temperature value that has the highest overlap during a given time period. The highest and lowest normal corrected skin temperatures, which are designated as T_normal_high and T_normal_low, respectively, are determined by either highest or lowest repeated temperatures for more than 30 minutes but within 3 hours in the present examples. But the repeated values for T_normal_high and T_normal_low may not vary by more than 0.5° C. from T_normal in order to be considered "normal" temperature. It is understood that the time parameters as well as the temperature variability limitation may be adjusted and optimized depending on the circumstances, and is not limited to the time parameters and the temperature variability limitation exemplified herein.

Figure 6:
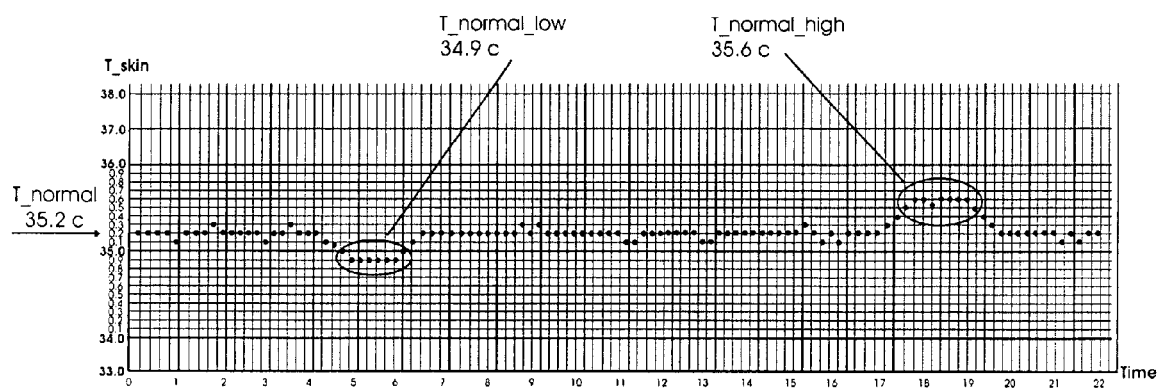
FIG. 6 shows a corrected skin temperature chart of a 3 year-old baby recorded by the baby monitoring device. The measured normal corrected skin temperature is 35.2° C. while the lowest normal corrected skin temperature is 34.9° C. at around 5-6 am and the highest normal corrected skin temperature is 35.6° C. at around 6-7 pm.

FIG. 6 is a temperature profile chart of a 3 year-old baby recorded by THE MONITORING DEVICE. As shown in FIG. 6, the measured normal skin temperature is 35.2° C. while the lowest and highest temperatures are 34.9° C. at around 5~6 AM and 35.6° C. at around 6~7 PM. This entire temperature profile is repeated every day, and thus a more consistent corrected skin temperature is determined as the temperature is measured continuously and repeatedly at the same time, resulting in less probability of erroneous designation of the normal corrected skin temperature at that time of day or under any particular environmental conditions. Each measured temperature is recorded in EEPROM.

There are three major advantages to this method. First, one can find an accurate normal corrected skin temperature of a baby, its highest and lowest normal corrected skin temperatures, and the time periods of the normal corrected skin temperature change. Second, the T_normal temperature is independent from the body temperature change, and as a result, provides its own level of stability, consistency and reliability for use in the present invention. Third, the temperature measurement is not affected by position of the monitoring device on the wearer.

Figure 7:
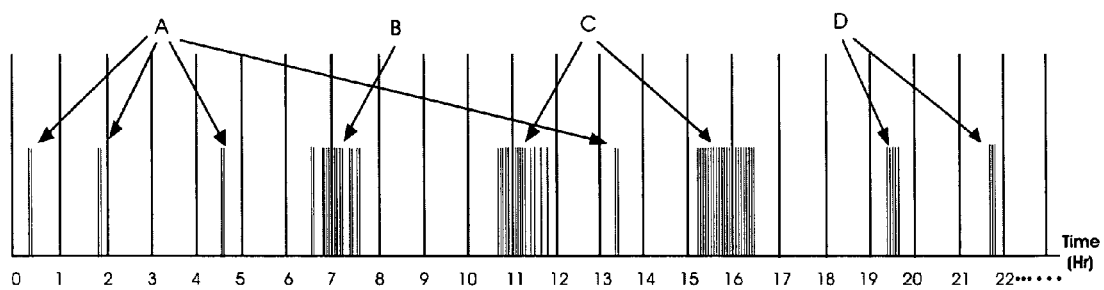
FIG. 7 shows a baby movement profile with sections A-D showing various movement patterns.

FIG. 7 displays movement patterns recorded from the movement sensor on a device worn by a baby. The generated signals shown in FIG. 7A is discarded as being "noise" or ignored for recordation, and is treated as non-movement during the time period because the detection signal is for a short time, and the intervals between the signals are very long, which may be more than 12 minutes in this example. An interpretation for this type of movement pattern is that the baby is randomly stirring during sleep. However, in FIG. 7B, the movement patterns are significant and are recorded because the intervals between the signals lie between 5 and 12 minutes even though the signal time may be short, which qualify in this example as being a significant state. If the detection interval is less than 5 minutes, as in FIG. 7C, the interval time "gap" is ignored, and the entire time period is considered to be an active time period. Thus, a reading which shows that within a given time period, two blocks of time consisting of active moments interspersed with short intervals of less than 5 minutes, which time blocks are separated by an interval gap of more than 12 minutes, as in FIG. 7D, is also considered to be significant and is recorded.

Figure 8:
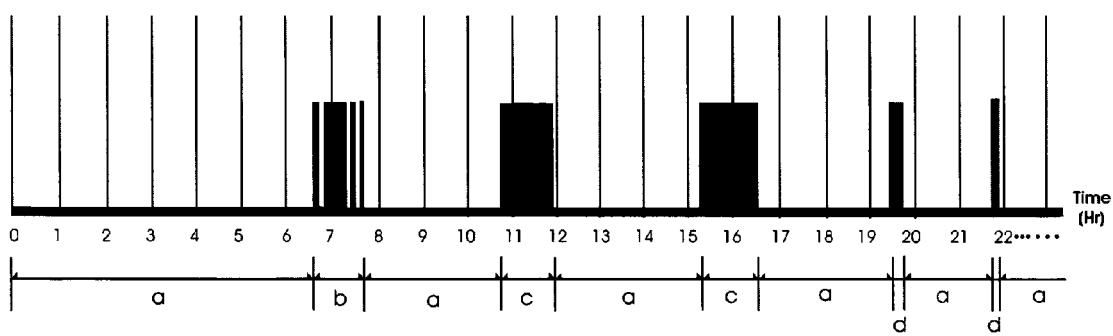
FIG. 8 shows a consolidated profile of the baby movement profile of FIG. 7.

FIG. 8 shows an analytical result of FIG. 7. From this chart, it is possible to determine the sleeping and activity times of a baby wearing the device comprising the motion detector. Data collected from the movement sensor are initially stored in EEPROM of THE MONITORING DEVICE. The data are used in the event of transmission or infection pattern analysis. The data may be stored indefinitely.

Analyzing the time period sections of FIG. 8, one interpretation of the time period of section A may be that this is the baby's sleeping time, and that the activity was caused by random movement; section B indicates that the baby is stirring during sleep, and may indicate that the baby is not sleeping well; section C indicates that the baby is awake and is active; and section D is consistent with baby's activity during nursing. In section D, the baby was sleeping for a few hours before section D, was awakened and nursed for about 20 minutes (first solid block of activity), and the baby was put back to sleep for another few hours.

Figure 9:
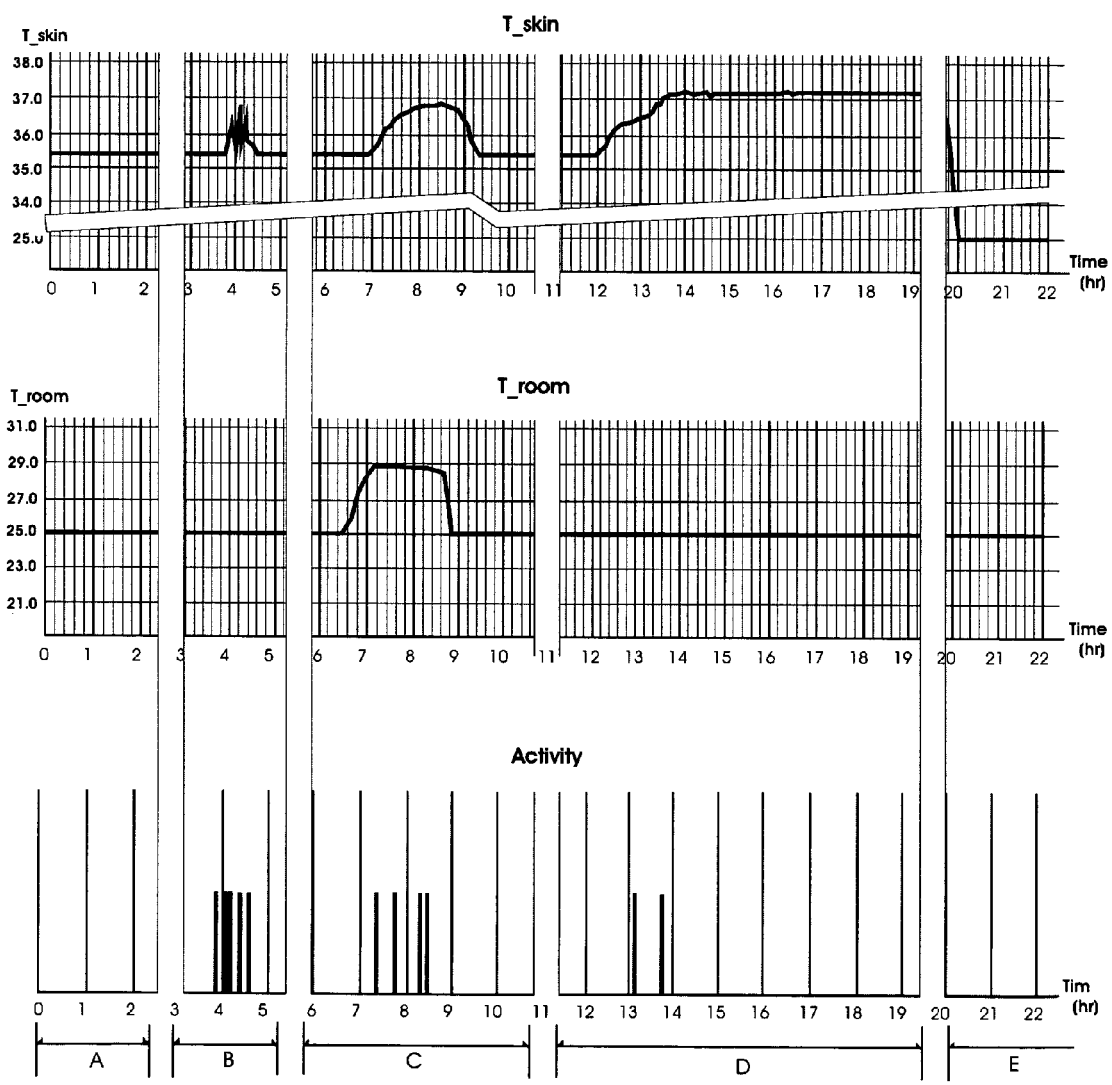
FIG. 9 shows time-correlated profiles of corrected skin temperature (T_skin); ambient temperature (T_room); and movement, which are divided into sections A-E.

FIG. 9 shows three correlated charts, which provide a relationship between the baby's corrected skin temperature profile, ambient temperature profile, and baby's movement profile during a specified, coordinated time period. Comparing these charts, one can learn the condition of a baby (for convenience, immediate surrounding humidity and baby's sweat are ignored).

Referring to FIG. 9, and the indicated sections,

A: The corrected skin temperature (T_skin) is normal. There is substantially no activity. Therefore, this is a condition in which the baby is sleeping.

B: There is a brief spike or irregular temperature rise in T_skin with corresponding sudden spike of activity. In a period of about 30 minutes, the corrected skin temperature fluctuates with frequent activity or movement. This is probably caused by agitation or stress for the baby. For example, the baby may be hungry.

C: The corrected skin temperature rises and falls, as does the ambient temperature in a span of about 20 minutes. The rise and fall of the corrected skin temperature lags behind the rise and fall of the ambient temperature. There is also a slight stirring by the baby. This is a condition in which the change in the baby's corrected skin temperature is due to the corresponding change in the ambient temperature. The baby is normal.

D: This is a condition in which the corrected skin temperature rises according to a pattern even though the ambient temperature is substantially level or constant. Also, there is only slight movement by the baby. This type of condition typically indicates the presence of an infection. Some activity is detected during the early stages of the infection when the corrected skin temperature is rising. The baby is sick.

E: This is a control. THE MONITORING DEVICE is separated from the baby. The corrected skin temperature (T_skin) reaches that of ambient temperature (T_room). In this case, THE MONITORING DEVICE is automatically converted to stand-by mode after 30 minutes.

FIGS. 10A-10E show a variety of indicative conditions of a baby on the display screen. Therefore, a parent's immediate judgment is possible because THE MONITORING DEVICE displays the baby's condition on the display screen.

FIG. 10A shows a normal condition. Several environmental measurements and information regarding standard values for height and weight, for instance at that age are displayed.

FIG. 10B shows where bad environmental factors, such as high or low humidity and temperature, are not safe for a baby. THE MONITORING DEVICE may simply give a warning by sound.

FIG. 10C shows a situation where a baby has a slight fever but the condition is not serious. It is necessary to observe the baby carefully for a few days.

FIG. 10D shows that the baby is under stress. However, the cause of the rising temperature may come from an infection. It is advised to watch the baby carefully for a few days.

FIG. 10E shows a critical condition because the corrected skin temperature is too high. Immediate action is necessary. Instead of showing an icon on the LCD screen, a message is directly displayed with a continuous warning sound. In this situation, it sends a message to parent's or doctor's cell phone through a modem in the computer at home. In addition, THE MONITORING DEVICE may display information on what to do. For example, the display may say to wash the baby with warm water or give the baby non-aspirin type fever reducer.

Figure 11:
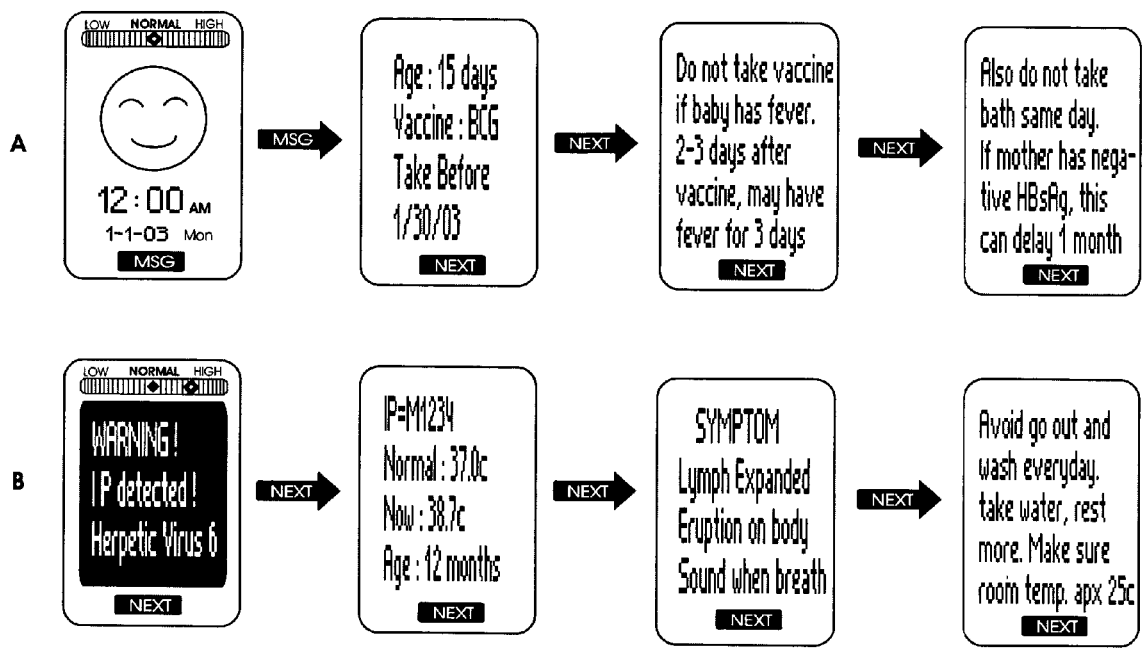
FIGS. 11A-11B show various icons that may be displayed on the baby monitoring device to show health condition of the baby.

FIGS. 11A-11B show displays of types of health information given by THE MONITORING DEVICE.

FIG. 11A shows an example regarding immunization. It displays pre-cautionary information before immunization and some possible symptoms after immunization. FIG. 11B shows infection pattern for Herpes Virus 6 infection. The display may provide information on its symptoms and advise folk remedies. EEPROM of THE MONITORING DEVICE contains important data for baby care, such as immunization and infection pattern. Thus, THE MONITORING DEVICE displays action notice on its LCD screen whenever it is necessary. When the monitoring device is used with computer at home, it is possible to increase the number of functions of the monitoring system.

Example 2

Software and Computer Used at Home

Computer software is installed in computer at home optionally equipped with a wireless network system. Information regarding a baby is transmitted directly or through wireless communication from THE MONITORING DEVICE, and is stored in a memory device of a computer where computer at home is installed so that it is possible to perceive the changes in the baby's condition over a long time period. All childcare information may be automatically displayed on the computer screen based on the baby's age. In addition, new childcare information can be periodically updated through an online service, which is connected to the monitoring system main server. Parents who have the monitoring system can share childcare information or infectious disease alert through online. This information sharing is expected to be helpful for nursing or childcare.

Additional functions for the computer at home may include the capability to automatically turn on music to draw baby's attention when the baby is agitated or is under stress. Or, a message can be sent to parent's cell phone or e-mail whenever there is an emergency. In addition, parents can receive various messages regarding regular checkup or immunization schedule for their children from an associated clinic that is linked within the monitoring system. Appointment with a doctor may be made online as well.

In another aspect, it is also important to safely keep a child's medical records. These records are especially necessary when a child attends school for the first time. When going to a doctor's office, it is desirable to bring a child's medical records. In general, doctors recommend that parents keep a child's medical records for 20 years. A child's medical records in a COMPUTER AT HOME may be automatically updated by a computer at hospital or in a doctor's office after a medical examination or immunization visit.

Since it is essential to have a doctor's signature on a child's medical records, the doctor's signature file is also attached whenever the child's medical records in COMPUTER AT HOME are updated. The doctor's signature verification can be performed by using a similar method as with credit card authorization done online.

When one needs to change a doctor's office, the medical information of the child can be transferred from one office to the other electronically by using COMPUTER AT HOME. All of the childcare information is automatically registered in the COMPUTER AT HOSPITAL of the new doctor's office. If necessary, a hardcopy of the child's medical records can be printed out at any time.

Example 3

Repeater

Repeater is a connecting device between THE MONITORING DEVICE and COMPUTER AT HOME with a few enhanced functions. For example, piezo transducer of THE MONITORING DEVICE has a weak sound volume whereas a speaker on the repeater can produce louder warning sound. In addition, the repeater can have a larger LCD screen than THE MONITORING DEVICE. Repeater uses a wireless network standard so that it can communicate with a computer equipped with a wireless network system. Thus, in one aspect of the invention, it can instruct a computer to turn on music or video camera so that one can see a baby on a computer monitor. The repeater can be operated by simply plugging it into an electrical outlet. However, the repeater may also be battery operated.

Figure 12:
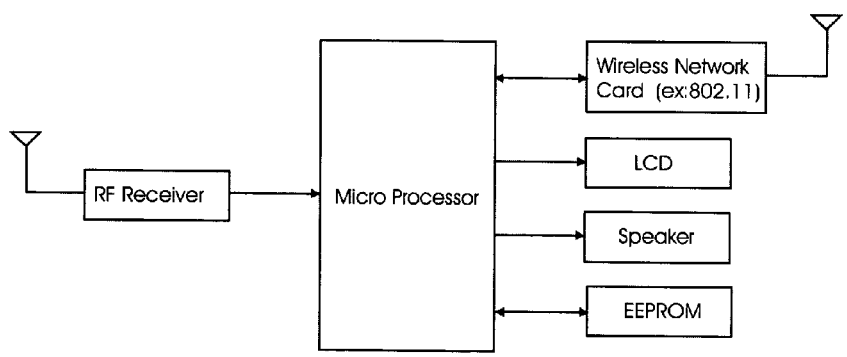
FIG. 12 shows a block diagram of a repeater.

FIG. 12 shows a block diagram of a repeater.

Example 5

Software and Computer Used at Hospital

When a child with THE MONITORING DEVICE visits a doctor's office, a child's medical information can be wirelessly transmitted to COMPUTER AT HOSPITAL by using switches shown in FIG. 2(6). THE MONITORING DEVICE transmits all information of a child including birth date, gender, blood type, address, and all recorded temperature and activity profiles within last 30 days while COMPUTER AT HOSPITAL searches a database and looks for the corresponding record of the child. This process ultimately minimizes unnecessary paperwork in a doctor's office. In this case, THE MONITORING DEVICE also plays a role as an identification tag or barcode for a child.

Since the transmitted data contain information for at least the last 30 days, all of the sensor data of a sick child may be added after the outbreak of illness as well as during the incubation and transition periods.

Because COMPUTER AT HOSPITAL may provide a detailed analysis of a baby's condition, including reliable data regarding condition of the baby before the outbreak, doctors now have the capability to more accurately diagnose an illness.

Besides these main functions, COMPUTER AT HOSPITAL may have several additional functions, such as allowing for advertisement, making appointments, rendering medical advice on line, and general information about the doctor's office.

As disclosed above, the monitoring system has almost complete information for childcare and it also has a function to grasp health condition of a baby at various stages.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A baby health monitoring device worn by a baby comprising:
   (i) a skin temperature sensor connected to a microprocessor which mathematically converts the sensed temperature to corrected skin temperature;
   (ii) a movement sensor;
   (iii) a display screen; and
   (iv) a means for communicating with a computer, wherein the baby health monitoring device is a single unit.

2. The device according to claim 1, comprising a humidity sensor.

3. The device according to claim 1, which is shaped as a band.

4. A baby health monitoring system comprising the device according to claim 1 connected to a repeater, which is connected to a computer at home comprising software designed to communicate with the device.

5. The system according to claim 4, wherein said device, repeater and computer at home are connected wirelessly.

6. The system according to claim 5, wherein the computer is connected to a web server so as to be in communication with other computers at home or computers at hospital.

7. A method of facilitating determination of health of a baby comprising simultaneously monitoring corrected skin temperature of the baby, monitoring ambient temperature surrounding the baby, and monitoring level of movement of the baby with the device according to claim 1 over time; and comparing and analyzing data obtained, wherein presence of high or rising corrected skin temperature compared with substantially level ambient temperature and substantially infrequent movement indicates that the baby is not healthy.

8. The method according to claim 7, wherein the instructions are in written form.

9. The method according to claim 7, wherein the instructions are transmitted by broadcast.

10. A chart comprising corrected skin temperature profile over a set time period, wherein the corrected skin temperature is generated and recorded by comparing and analyzing data obtained with the device according to claim 1.

11. The chart according to claim 10, comprising ambient temperature profile over the set time period.

12. The chart according to claim 11, comprising a movement profile over the set time period.

13. The chart according to claim 10, which is displayed on a solid medium.

14. The chart according to claim 13, which is displayed on a screen.

15. The chart according to claim 13, which is paper.

16. A method of facilitating determination of health of a baby comprising reviewing and analyzing the chart according to claim 12, and comparing corrected skin temperature profile, ambient temperature profile, and movement profile, wherein presence of high or rising corrected skin temperature compared with substantially level ambient temperature and substantially infrequent movement indicates that the baby is not healthy.

17. A method of determining an infection in a baby, comprising reviewing and analyzing the chart according to claim 12, to determine a pattern of rise or fall in corrected skin temperature, which indicates presence of an infection.

18. A method of identifying a viral infection pattern comprising reviewing and analyzing a corrected temperature profile, ambient temperature profile and movement profile of a baby and comparing with an established profile, wherein the corrected temperature, ambient temperature, and movement profiles are generated and recorded as a result of comparing and analyzing data obtained with the device according to claim 1.

19. The method according to claim 18, wherein the established profile is provided by a computer at home or computer at hospital, and stored in a common server that links computer at home and computer at hospital.

20. A method of identifying early onset of a viral infection comprising reviewing and analyzing a corrected temperature profile, ambient temperature profile and movement profile of a baby and comparing with an established profile, wherein the corrected temperature, ambient temperature, and movement profiles are generated and recorded by comparing and analyzing data obtained with the device according to claim 1, and matching profile indicates early onset of the viral infection.

21. The baby health monitoring device according to claim 1, wherein the display screen displays the corrected skin temperature.

* * * * *